United States Patent
Deng et al.

(10) Patent No.: US 11,957,098 B2
(45) Date of Patent: Apr. 16, 2024

(54) METHOD OF CULTIVATING LC-PUFA CONTAINING TRANSGENIC BRASSICA PLANTS

(71) Applicant: BASF PLANT SCIENCE COMPANY GMBH, Ludwigshafen (DE)

(72) Inventors: Xinmin Deng, Eden Prairie, MN (US); Kristin Gray, Fort Collins, CO (US); Jakir Hasan, Great Falls, MT (US); Keith Horton, Great Falls, MT (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 17/046,989

(22) PCT Filed: Apr. 11, 2019

(86) PCT No.: PCT/US2019/027015
§ 371 (c)(1),
(2) Date: Oct. 12, 2020

(87) PCT Pub. No.: WO2019/200118
PCT Pub. Date: Oct. 17, 2019

(65) Prior Publication Data
US 2021/0153447 A1 May 27, 2021

Related U.S. Application Data

(60) Provisional application No. 62/657,128, filed on Apr. 13, 2018.

(51) Int. Cl.
*C12N 15/82* (2006.01)
*A01H 1/00* (2006.01)
*A01H 5/10* (2018.01)
*A01H 6/20* (2018.01)

(52) U.S. Cl.
CPC ............... *A01H 1/105* (2021.01); *A01H 5/10* (2013.01); *A01H 6/202* (2018.05)

(58) Field of Classification Search
None
See application file for complete search history.

(56) References Cited

U.S. PATENT DOCUMENTS

| | | | |
|---|---|---|---|
| 7,807,849 B2 | 10/2010 | Singh | |
| 8,088,906 B2* | 1/2012 | Qiu | A61P 35/02 536/23.2 |
| 9,453,183 B2 | 9/2016 | Singh et al. | |
| 2010/0222605 A1 | 9/2010 | Stiewe et al. | |

FOREIGN PATENT DOCUMENTS

| | | |
|---|---|---|
| WO | 2004071467 A3 | 8/2004 |
| WO | 2013153404 A1 | 10/2013 |
| WO | 2015089587 A1 | 6/2015 |
| WO | 2016075303 A1 | 5/2016 |
| WO | 2016075325 A4 | 5/2016 |
| WO | 2016075327 A2 | 5/2016 |
| WO | 2017023734 A1 | 2/2017 |
| WO | WO-2017194728 A1 | 11/2017 |
| WO | 2017210426 A1 | 12/2017 |

OTHER PUBLICATIONS

Usher et al, Metabolic Engineering Communications 2: 93-98, 2015 (Year: 2015).*
Zheng et al, Plant Cell Envir 34 (9): 1431-1442, 2011 (Year: 2011).*
Williams et al, Plant Physiol 87: 904-910, 1988 (Year: 1988).*
Yaniv et al, Industrial Crops and Products 3: 247-251, 1995 (Year: 1995).*
"International Application Serial No. PCT/US2019/027015, International Search Report dated Jul. 19, 2019", 2 pgs.
"International Application Serial No. PCT/US2019/027015, Written Opinion dated Jul. 19, 2019", 5 pgs.
Han et al., "High level accumulation of EPA and DHA in field-grown transgenic Camelina—a multi-territory evaluation of TAG accumulation and heterogeneity," Plant Biotechnology Journal, 2020, 18, p. 2280-2291.
O'Quin et al., "Temperature-sensitive post-translational regulation of plant omega-3 fatty acid desaturases is mediated by the endoplasmic reticulum-associated degradation pathway," The Journal of Biological Chemistry, 2010, 285(28), p. 21781-21796.
Chapman et al., "Commentary: Why don't plant leaves get fat?," Plant Science, 2013, 207, p. 128-134.
Deng et al., Temperature effects on fatty acid composition during development of low-linolenic oilseed rape (*Brassica napus* L.).
Xu et al., "Triacylglycerol metabolism, function, and accumulation in plant vegetative tissues," Annu. Rev. Plant Biol., 2016, 67, p. 179-206.
Pokharel et al., "High night-time temperature during flowering and pod filling affects flower opening, yield and seed fatty acid composition in conola," Journal of Agronomy and Crop Science, 2020, 206, p. 579-596.

(Continued)

*Primary Examiner* — Vinod Kumar
(74) *Attorney, Agent, or Firm* — MARSHALL, GERSTEIN & BORUN LLP

(57) ABSTRACT

Various embodiments disclosed relate to increasing the proportion of omega-3 fatty acid in seed oil produced by a plurality of *Brassica* plants, such as canola, transgenically modified to produce seed oil comprising at least one of EPA, DHA and DPA. Transgenic *Brassica* plants, such as transgenic canola, are subjected to an environment which has an average daily day-night temperature difference of at least 13° C. during the transgenic plant's period of seed maturation. The seed oil is at least 5 wt % EPA. The seed oil is at least 1 wt % DPA. The seed oil is at least 0.2 wt % DHA. The seed oil is at least 5.2 wt % a mixture of EPA and DHA. The seed oil is at least 6 wt % long chain omega-3 fatty acids.

13 Claims, 1 Drawing Sheet

(56) References Cited

OTHER PUBLICATIONS

Borges et al., "Forecasting Brassica napus production under climate change wiht a mechanistic species distribution model," Scientific Reports, 2013, 13, p. 12656.
Zhou et al., "Effect of high night temperature on storage lipids and transcriptome changes in developing seeds of oilseed rape," Journal of Experimental Botany, 2018, 7, p. 1721-1733.

* cited by examiner

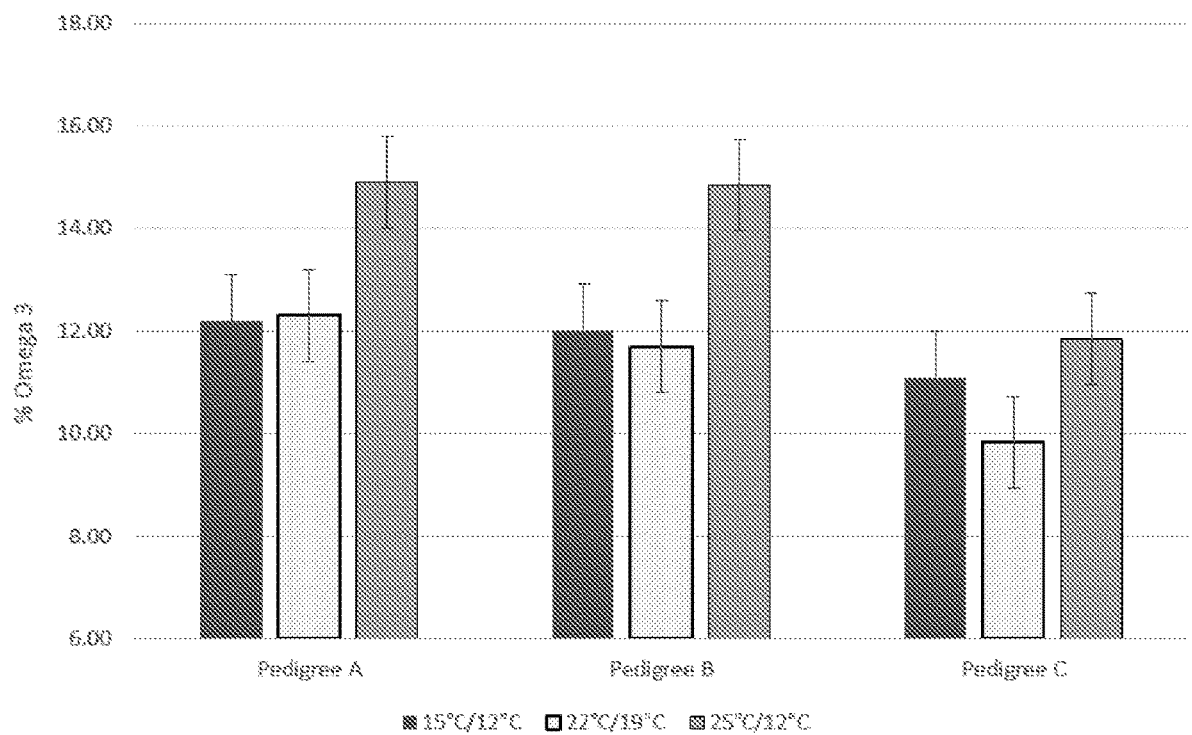

METHOD OF CULTIVATING LC-PUFA CONTAINING TRANSGENIC BRASSICA PLANTS

CROSS-REFERENCE TO RELATED APPLICATIONS

This application is a U.S. National Stage Filing under 35 U.S.C. 371 from International Application No. PCT/US2019/027,015, filed 11 Apr. 2019, and published as WO 2019/200,118 on 17 Oct. 2019, which application claims the benefit of U.S. Provisional Patent Application Ser. No. 62/657,128, filed 13 Apr. 2018, entitled "METHOD OF CULTIVATING LC-PUFA CONTAINING TRANSGENIC BRASSICA PLANTS" which applications are hereby incorporated by reference herein in their entirety.

BACKGROUND

Omega-3 fatty acids are polyunsaturated fatty acids which convey a range of health benefits and essential to healthy development in humans and other animals. Farmed fish provide humans with an important dietary source of omega-3 fatty acids, but fish also require omega-3 fatty acids, particularly long-chain omega-3 fatty acids which would typically be obtained from marine sources in the wild. Aquaculture currently consumes what amounts to a majority of the global supply of omega-3 fatty acids. Historically, farmed fish were provided feed obtained from marine sources to deliver required nutrients. However, providing farmed fish with nutrients sourced from wild marine sources may exacerbate declining wild fish populations and stress other ocean resources. Although certain omega-3 fatty acids are readily available from plant sources, plant-based diets typically fail to provide sufficient dietary amounts of the type of long chain omega-3 fatty acids found in marine oils. Long chain omega-3 fatty acids include EPA (eicosapentaenoic acid), DPA (docosapentaenoic acid) and DHA (docosahexaenoic acid). Other sources of long chain omega-3 fatty acids include microalgae or production via bioreactors.

Recently, new terrestrial, plant-based sources of long chain omega-3 fatty acids have been described. For example, Oilseed plants, such as canola and other Brassica plants, have been genetically modified to provide long chain omega-3 fatty acids including EPA, DPA and DHA (WO 2016/075303, WO 2016/075325, WO 2016/075327, WO 2015/089587, WO 2013/153404, WO 2004/071467 and U.S. Pat. No. 7,807,849 B2). Such plant-sourced omega-3 fatty acids can be used alone or together with marine-sourced omega-3 fatty acids to supplement or wholly provide a dietary source of omega-3 fatty acids, including long chain omega-3 fatty acids (WO 2017/210426). Transgenic canola can be a scalable, plant-based source of long chain omega-3 fatty acids. Such plants have the advantage of providing a source of long chain omega-3 fatty acid that does not disrupt or deplete natural marine resources.

Canola is an important Brassica plant crop is an affordable and healthy source of dietary oil. Canola plants are grown globally and harvested for their seeds which have a high oil content. For example, canola seeds can contain 44% oil, which is double the oil content of soybeans. As canola plants mature, they produce yellow flowers and seed pods which gradually change in color from green to pale yellow and then tan. Each seed pod is filled with seeds which turn from translucent to green and then black. The seeds are harvested, and oil is extracted therefrom.

Approximately 35-45 days after first flower of the canola plants, seed filling of seed pods may be complete. By 40 days after first flower, the seeds can fully change color. However, as seed pods mature, they become brittle and prone to shattering. A major disadvantage of canola is that the plant is physically vulnerable to weather and elements. Frost can be destructive to canola seeds and mature seed pods can shatter. If canola plants remain on the field for too long, they are subject to an increasing risk of being afflicted with disease, frost or physically battered such that the seed pods shatter and the crop is destroyed. The longer canola plants remain unharvested, the more likely it is that the crop will be lost. For these reasons, Canola producers seek to harvest as early as possible to avoid loss.

To avoid shattering and loss of the crop, canola can be harvested by direct combining within 40-45 days from first flower. Canola can also be harvested by swathing and doing so is popular is it permits harvesting 8 to 10 days earlier than direct combining. Swathing involves cutting the crop and forming windrows that can be laid on the cut stubble. Swathed canola crops dry and cure in the field and are better protected from shattering than uncut crops. Swathed canola sees some further color change of seeds, but once swathed the plants produce no further seeds and seeds will not accumulate more nutrients. Swathing can be performed when 30% to 40% or up to 60% of seeds have changed color from green to black.

SUMMARY OF THE DISCLOSURE

The present disclosure provides a method of increasing long-chain omega-3 fatty acid production in transgenic Brassica oilseed plants, such as canola plants. The present disclosure also provides a method of cultivating transgenic Brassica oilseed plants. The present disclosure further provides transgenic Brassica seeds having an increased proportion of omega-3 fatty acid. The present disclosure advantageously provides seed oil having an increased long chain omega-3 fatty acid fraction.

The present disclosure provides a method of increasing the proportion of long-chain omega-3 fatty acid in seed oil produced by a plurality of transgenic Brassica oilseed plants, comprising subjecting the transgenic Brassica oilseed plants to an environment which has an average daily day-night temperature difference of at least 13° C. during a period of seed maturation for the transgenic canola plants; and wherein the transgenic Brassica oilseed plants have been transgenically modified to produce seed oil comprising at least one of EPA, DHA and DPA.

The present disclosure provides a method of cultivating a plurality of transgenic Brassica oilseed plants, such as canola plants, comprising growing the plants in an environment which has an average daily day-night temperature difference of at least 7° C. during a period of seed maturation for the transgenic canola plants; and wherein the transgenic canola plants produce seeds comprising at least one of EPA, DHA and DPA.

The present disclosure also provides Brassica plant seeds comprising seed oil which is at least 17 wt % long chain omega-3 fatty acids.

Advantages, some of which are unexpected, are achieved by various embodiments of the present disclosure. For example, methods of the present disclosure may have the advantage of increasing desired omega-3 fatty acids as a percentage of the oil produced by transgenic oilseed plants. Methods described herein may have the advantage of producing a larger total amount of omega-3 fatty acids per transgenic oilseed plant. Methods of the present disclosure may also have the advantage of producing a larger total amount of omega-3 fatty acids per square foot of area growing the oilseed plant. Methods of the present disclosure may further have the advantage of providing oilseeds and seed oil which is more cost effectively processed, with less waste, to produce oil products having a higher concentration of omega-3 fatty acids. Methods of the present disclosure may have the advantage of producing a crop of plants with seeds having improved consistency with respect to the amount of omega-3 fatty acids in the seeds and seed oil. The present disclosure advantageously provides seeds and seed oil having a high concentration of omega-3 fatty acids. Such seeds and seed oil having a high concentration of omega-3 fatty acids can be diluted with other seeds and seed oil to readily provide an oil product having a desired amount of omega-3 fatty acids and other fatty acids. In various embodiments, the present disclosure has the advantage of providing a non-marine or plant-based source of omega-3 fatty acids. In various embodiments, these advantages relate to desired long chain omega-3 fatty acids or, further, one or more specific desired long chain omega-3 fatty acids such as DHA, EPA and DPA.

BRIEF DESCRIPTION OF THE DRAWINGS

FIG. 1 shows a plot depicting the effect of day-night temperature during seed maturation on % omega-3 fatty acid accumulation in three transgenic canola hybrids.

DETAILED DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Any publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Definitions of particular terms may be contained within this section or may be incorporated into the sections of text below.

A "plurality" refers to any group having two or more members. A plurality of plants thus can be a group of 2 or more plants, a group of 10 or more plants, a group of 100 or more plants, a group of 1,000 or more plants, a group of 10,000 or more plants, a group of 100,000 or more plants, or a group of 1,000,000 or more plants. A plurality of plants can also be from 2 to 10 plants, from 2 to 100 plants, from 10 to 100 plants, from 100 to 1,000 plants, from 1,000 to 10,000 plants, from 10,000 to 100,000 plants, from 100,000 to 1,000,000 plants, from 1,000,000 to 10,000,000 plants.

The term "day" and "daily" as used herein refers to a 24-hour period. In various embodiments, the 24-hour period is a calendar day.

The term "daily day-night temperature difference" as used herein refers to the difference in air temperature between the average daytime air temperature and the average nighttime air temperature occurring within a day. In various embodiments, the day may be any 24-hour period. In various embodiments, the day may be a calendar day.

The term "daily high-low temperature difference" as used herein refers to the difference in air temperature between the highest air temperature and the lowest air temperature occurring within a day. In various embodiments, the day may be any 24-hour period. In various embodiments, the day may be a calendar day.

The term "average daily day-night temperature difference" as used herein refers to an average (mean) difference calculated from all of the daily day-night temperature differences corresponding to each day in the specified period. The specified period may be the seed maturation period. As an example, an average daily day-night temperature difference for a 45-day period after first flower, would be calculated by summing all of the daily day-night temperature differences for the 45-day period and dividing by 45.

The term "first flower" as used herein in the context of a single plant refers to the date upon which that plant blooms its first flower. "First flower" as used in the context of a field of plants means the date upon which at least 10% of the plants in the field have at least one flower blooming.

The term "minimum daily day-night temperature difference" as used herein refers to the smallest daily day-night temperature difference from entire group of daily day-night temperature differences corresponding to each day in the specified period.

The term "nighttime low temperature" as used herein refers to the low air temperature occurring during the time between sunset and sunrise, inclusive.

The term "daytime high temperature" as used herein refers to the high air temperature occurring during the time between sunrise and sunset, inclusive.

The term "oil" as used herein can refer to a substance formed primarily of fatty acids. An oil herein may be either liquid or solid at room temperature and may be in liquid or solid form (e.g. a dry fat). Oils can refer be formed primarily of fatty acids, for instance in triglyceride or phospholipid (e.g. lecithins) form. Examples of oils herein include various vegetal oils such as *Brassica* oils as well as marine oils such as fish oil or hill oil, animal fats such as poultry fat, and phospholipids such as soy lecithin. Oils may also include other compounds often associated with fats such as sterols, e.g. cholesterol, or tocopherols.

The term "fatty acid" as used herein can refer to a molecule comprising a hydrocarbon chain and a terminal carboxylic acid group. As used herein, the carboxylic acid group of the fatty acid may be modified or esterified, for example as occurs when the fatty acid is incorporated into a glyceride or a phospholipid or is attached to another molecule such as acetyl-CoA (e.g., COOR, where R refers to, for example, a carbon atom). Alternatively, the carboxylic acid group may be in the free fatty acid or salt form (i.e., COO⁻ or COOH).

A "saturated" fatty acid is a fatty acid that does not contain any carbon-carbon double bonds in the hydrocarbon chain. An "unsaturated" fatty acid contains one or more carbon-carbon double bonds. A "polyunsaturated" fatty acid contains more than one such carbon-carbon double bond while a "monounsaturated" fatty acid contains only one carbon-carbon double bond. Carbon-carbon double bonds may be in one of two stereoconfigurations denoted cis and trans. Naturally-occurring unsaturated fatty acids are generally in the "cis" form. Unsaturated fatty acids may, for example, be of the omega-6 (or n-6 or ω-6) or omega-3 (n-3 or ω-3) type. Omega-6 fatty acids have a first double bond at the sixth position from the methyl end of the fatty acid chain while omega-3 fatty acids have a first double bond at the third position from the methyl end of the chain. The term "long-chain" when applied to an omega-3 or omega-6 fatty acid means having a chain of 20 carbons or more.

Fatty acids found in plants and oils described herein may be incorporated into various glycerides. The terms "triacylglycerol," "triglyceride," and "TAG" are used interchangeably herein to refer to a molecule comprising a glycerol that is esterified at each of its three hydroxyl groups by a fatty acid and thus, comprises three fatty acids. The terms "diacylglycerol," "diglyceride," and "DAG" refer to a molecule comprising a glycerol esterified by a fatty acid at only two of its three available hydroxyl groups, such that it contains only two fatty acids. Likewise, the term "monoglyceride" refers to a glycerol modified by a fatty acid at only one of the available three hydroxyl groups so that it comprises only one fatty acid.

Fatty acids found in plants and oils described herein may also be incorporated into various "phospholipids," abbreviated "PL" herein. Phospholipids are molecules that comprise a diglyceride, a phosphate group, and another molecule such as choline ("phosphatidyl choline;" abbreviated "PC" herein), ethanolamine ("phosphatidyl ethanolamine;" abbreviated "PE" herein), serine "phosphatidyl serine;" abbreviated "PS" herein), or inositol ("phosphatidyl inositol;" abbreviated "PI" herein). Phospholipids, for example, are important components of cellular membranes.

The levels of particular types of fatty acids may be provided herein in percentages out of the total fatty acid content of an oil. Unless specifically noted otherwise, such percentages are weight percentages based on the total fatty acids, TAGs, or PLs in the oil component, respectively, as calculated experimentally. Thus, for example, if a percentage of a specific species or set of fatty acids is provided, e.g., EPA or EPA+DHA or EPA+DPA+DHA, this is a w/w percentage based on the total fatty acids detected in the oil. The fatty acid composition of an oil can be determined by methods well known in the art. The American Oil Chemist's Society (AOCS) maintains analytical methods for a wide variety of tests performed on vegetable oils. Hydrolysis of the oil's components to produce free fatty acids, conversion of the free fatty acids to methyl esters, and analysis by gas-liquid chromatography (GLC) is the universally accepted standard method to determine the fatty acid composition of an oil sample. The AOCS Procedure Ce 1-62 describes the procedure used.

The term "polyunsaturated fatty acids" and "PUFA" as used herein refers to fatty acids comprising at least two double bonds. PUFA may comprise three, four, five or six double bonds. PUFA may comprise, for example, from 18 to 24 carbon atoms in the fatty acid chain. Long chain PUFA ("LC-PUFA) can have, for example, from 20 to 24 carbon atoms in the fatty acid chain.

The term "omega-3 fatty acid" includes fatty acid, and may also include derivatives thereof such as triglycerides, esters and phospholipids. An omega-3 fatty acid has multiple double bonds each separated by methylene linkages. Counting from the terminal (ω) carbon end of the fatty acid, a first double of an omega-3 fatty acid occurs between the third and fourth carbons from the terminal end. An omega-3 fatty acid may have, e.g., three double bonds, four double bonds, five double bonds or six double bonds. An omega-3 fatty acid may have all cis-double bonds. The term "long chain" omega-3 fatty acid as used herein refers to an omega-3 fatty acid having twenty (20) or more carbon atoms in the fatty acid chain.

The term "EPA" refers to an omega-3 fatty acid, all-cis-5,8,11,14,17-eicosapentaenoic acid, also represented as 20:5 (n-3). EPA is a long chain polyunsaturated fatty acid.

The term "DHA" refers to an omega-3 fatty acid, all-cis-4,7,10,13,16,19-docosahexaenoic acid, also represented as 22:6 (n-3). DHA is a long chain polyunsaturated fatty acid.

The term "DPA" refers to an omega-3 fatty acid, all-cis-7,10,13,16,19-docosapentaenoic acid, also represented as 22:5 (n-3). DPA is a long chain polyunsaturated fatty acid The term "ALA" refers to an omega-3 fatty acid all-cis-9,12,15-octadecatrienoic acid, also represented as 18:3 (n-3). ALA is a short chain polyunsaturated fatty acid.

The term "SDA" refers to an omega-3 fatty acid all-cis-6,9,12,15-octadecatetraenoic acid, also represented as 18:4 (n-3). SDA is a short chain polyunsaturated fatty acid.

The term "seed oil" or "oil from an oilseed plant" and related terms as used herein refer to an oil derived from seeds or other parts of an oilseed crop plant. In various embodiments, the oil also may be chemically treated or refined in various ways, for example by degumming, refining, bleaching, dewaxing, and/or deodorizing. The seed oil may be oil from *Brassica* oilseed plants. The seed oil may be oil from transgenic *Brassica* oilseed plants. The oil from an oilseed plant may be canola oil. In various embodiments, the oil includes one or more omega-3 fatty acids, such as, for example, EPA, DHA, DPA, ALA and SDA. The oil may include omega-3 fatty acids of eicosapentaenoic acid, docosahexaenoic acid and octadecatrienoic acid. The oil may also include one or more omega-6 fatty acids, such as, for example gamma-linolenic acid, linoleic acid, dihomogamma-linolenic acid and arachidonic acid. Seed produced by methods of the present disclosure may be used to produce a commodity product such as, but not limited to, seed oil. The term "commodity product" refers to any product that is sold to consumers. Seed produced by the methods described herein may thus be used for food, feed, fuel or other commercial or industrial purposes or for purposes of growing or reproducing the species.

The term "transgenic oilseed plant" as used herein can refer to a plant species which has been genetically modified to produce long-chain omega-3 fatty acids such as EPA, DPA, and/or DHA. The resulting oil can be referred to as an "oil from a transgenically modified oilseed plant" or by similar terms. The terms transgenic, transgenically modified, modified or genetically modified are used here to distinguish the long-chain omega-3 fatty acid producing plants, or the oils derived from such plants, from those of other plant lines that do not produce long-chain omega-3 fatty acids. Without being limited to theory, the plants may have been modified to express the enzymes needed for production of EPA, DPA, and DHA from precursor fatty acids. If the oilseed plant is, for example, a *Brassica* or *Camelina* species, then the terms "transgenic *Brassica* oilseed plants" or "transgenic *Camelina* oilseed plant" may be used. The "transgenic oilseed plant" may also be transgenically modified in additional ways, such as for herbicide resistance or to modify the proportions of certain other fatty acids in its oil, in addition to having been modified to produce long-chain omega-3 fatty acids such as EPA, DPA, and/or DHA. In various embodiments, the transgenic oilseed plant is compared to oilseed plant which has not been modified to produce long-chain omega-3 fatty acids such as EPA, DPA, and/or DHA. Such unmodified plant may yet still be a transgenic plant which has been modified in other ways, e.g., such as for herbicide resistance, but the plant is not modified such that it produces long-chain omega-3 fatty acids.

In various embodiments, the transgenic oilseed plants of the invention comprise event LBFLFK (ATCC designation PTA-121703). Seed and progeny of event LBFLFK are also encompassed in this embodiment. In another embodiment, the transgenic oilseed plants of the invention comprise event LBFDAU (ATCC designation PTA-122340). Seed and progeny of event LBFDAU are also encompassed in this embodiment. Such transgenic oilseed plants may be *Brassica* plants. Seeds of *Brassica* event LBFLFK (ATCC designation PTA-121703) and *Brassica* event LBFDAU (ATCC designation PTA-122340) have been deposited by applicant(s) at the American Type Culture Collection, Manassas, VA, USA, under the provisions of the Budapest Treaty on the International Recognition of the Deposit of Microorganisms for the Purposes of Patent Procedure. Applicants have no authority to waive any restrictions imposed by law on the transfer of biological material or its transportation in commerce. Applicants do not waive any infringement of their rights granted under this patent or rights applicable to the deposited events under the Plant Variety Protection Act (7 USC sec. 2321, et seq.), Unauthorized seed multiplication prohibited. This seed may be regulated according to national law. The deposition of seeds was made only for convenience of the person skilled in the art and does not constitute or imply any confession, admission, declaration or assertion that deposited seed are required to fully describe the invention, to fully enable the invention or for carrying out the invention or any part or aspect thereof.

The present disclosure may thus relate to plants LBFLFK and LBFDAU used to manufacture commodities typically acquired from *Brassica*. Seeds of LBFLFK and LBFDAU can be processed into meal or oil as well as be used as an oil source in animal feeds for both terrestrial and aquatic animals. The LC-PUFA-containing oil from events LBFLFK and LBFDAU may be used, for example, as a food additive to increase ω-3 fatty acid intake in humans and animals, or in pharmaceutical compositions to enhance therapeutic effects thereof, or as a component of cosmetic compositions, and the like.

The LC-PUFA produced by the LBFLFK and LBFDAU events and their progeny can include DHGLA, ARA, ETA, EPA, DPA and DHA. The VLC-PUFA produced by the LBFLFK and LBFDAU events and their progeny can include ARA, EPA, and DHA. The VLC-PUFA produced by the LBFLFK and LBFDAU events and their progeny can include EPA and/or DHA. The LBFLFK and LBFDAU events and their progeny can also produce intermediates of LC-PUFA which occur during synthesis. Such intermediates may be formed from substrates by the desaturase, keto-acyl-CoA-synthase, keto-acyl-CoA-reductase, dehydratase and enoyl-CoA-reductase activity of the polypeptides of the present invention. Such substrates may include LA, GLA, DHGLA, ARA, eicosadienoic acid, ETA, and EPA.

LBFLFK and LBFDAU plants can be bred by first sexually crossing a first parental *Brassica* plant grown from the transgenic LBFLFK or LBFDAU *Brassica* plant (or progeny thereof) and a second parental *Brassica* plant that lacks the EPA/DHA profile and imidazolinone tolerance of the LBFLFK or LBFDAU event, respectively, thereby producing a plurality of first progeny plants and then selecting a first progeny plant that displays the desired imidazolinone tolerance and selfing the first progeny plant, thereby producing a plurality of second progeny plants and then selecting from the second progeny plants which display the desired imidazolinone tolerance and EPA/DHA profile. These steps can further include the back-crossing of the first EPA/DHA producing progeny plant or the second EPA/DHA producing progeny plant to the second parental *Brassica* plant or a third parental *Brassica* plant, thereby producing a *Brassica* plant that displays the desired imidazolinone tolerance and EPA/DHA profile. It is further recognized that assaying progeny for phenotype is not required. Various methods and compositions, as disclosed elsewhere, can be used to detect and/or identify the LBFLFK or LBFDAU event. (See, e.g., WO 2016/075303).

Two different transgenic plants can also be sexually crossed to produce offspring that contain two independently-segregating exogenous genes. Selfing of appropriate progeny can produce plants that are homozygous for both exogenous transgenic inserts. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcos, ed., American Society of Agronomy, Madison Wis.

(1987), and Buzza, Plant Breeding, in *Brassica* Oilseeds: Production and Utilization. D. S. Kimber and D. I. McGregor eds. Cab International, Wallingford, UK (1995).

In various embodiments, the transgenic oilseed plants may encompass plants described in or prepared using methods described in WO 2016/075327, which describes EPA and DHA producing *Brassica* lines and how to produce such lines, among other embodiments. In various embodiments, the modified oilseed crop plants may encompass plants described in or prepared using methods described in WO 2016/075325, which describes modification of plant lipids containing PUFAs, among other embodiments. In various embodiments, the modified oilseed crop plants may encompass plants described in or prepared using methods described in WO 2016/075303, which describes *Brassica* events and progeny thereof. In various embodiments, the modified oilseed crop plants may encompass plants described in or prepared using methods described in WO 2015/089587, which describes EPA and DHA producing oilseed plants and how to produce such lines, among other embodiments. In various embodiments, the modified oilseed crop plants may encompass plants described in or prepared using methods described in WO 2004/071467, which describes EPA and DHA producing *Brassica* lines and how to produce such lines, among other embodiments. In various embodiments, the modified oilseed crop plants may encompass plants described in or prepared using methods described in U.S. Pat. No. 7,807,849 B2, which describes EPA and DHA producing *Arabidopsis* lines and how to produce such lines. In various embodiments, the modified oilseed crop plants may encompass plants described in or prepared using methods described in WO 2013/153404, which describes EPA and DHA producing *Camelina* lines and how to produce such lines. Each of these documents are incorporated by reference herein in their entirety for their disclosures of modified plant lines and how to produce such lines.

A transgenic "event" can be produced, for example, by transformation of plant cells with a heterologous DNA construct(s) including a nucleic acid expression cassette that comprises one or more transgene(s) of interest, the regeneration of a population of plants from cells which each comprise the inserted transgene(s) and selection of a particular plant characterized by insertion into a particular genome location. An event can be characterized phenotypically by the expression of the transgene(s). At the genetic level, an event can be part of the genetic makeup of a plant. The term "event" refers to the original transformant and progeny of the transformant that include the heterologous DNA. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA. As used herein, "insert DNA" can refer to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500 or 5000 base pairs or greater which is located either immediately upstream of and contiguous with, or immediately downstream of and contiguous with, the original foreign insert DNA molecule. Progeny of the *Brassica* LBFLFK event may comprise either LBFLFK Locus 1 or LBFLFK Locus 2, or both LBFLFK Locus 1 and LBFLFK Locus 2; progeny of the *Brassica* LBFDAU event may comprise either LBFDAU Locus 1 or LBFDAU Locus 2, or both LBFDAU Locus 1 and LBFDAU Locus 2. For examples of these events and others, and how such events can be incorporated into an oilseed crop, see WO 2016/075303, WO 2016/075325 and WO 2016/075327, each of which is incorporated by reference in its entirety.

As used herein, the term "*Brassica*" means any *Brassica* plant and includes all plant varieties that can be bred with *Brassica*. As defined herein, *Brassica* species include *B. napus, B. rapa, B. juncea, B. oleracea, B. nigra*, and *B. carinata*. In various embodiments, the *Brassica* species comprises the LBFLFK and LBFDAU events. In various embodiments, the *Brassica* species is *B. napus* comprising the LBFLFK and LBFDAU events, and progeny thereof. In various embodiments, the *Brassica* plant may be a canola plant. The *Brassica* plant may be a hybrid.

The term "canola" may refer to both canola plants and canola oil derived therefrom, depending on context. Canola as used herein is refers to the term's generic usage as a term for edible rapeseed oil and the plants from which they are derived, and also may refer to any codified usage of the term canola. For example, in various embodiments, canola may meet the following requirements: seeds of the genus *Brassica* (*Brassica napus, Brassica rapa* or *Brassica juncea*) from which the oil shall contain less than 2% erucic acid in its fatty acid profile and the solid component shall contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid (Canola Council of Canada). In various embodiments, canola may be any edible rapeseed oil or any plant from which edible rapeseed oil is derived. In various embodiments, canola may be an edible rapeseed oil, or a plant which produces such oil. In various embodiments, canola may be an edible rapeseed oil and also shall contain less than 2% erucic acid in its fatty acid profile, or a plant which produces such oil. In various embodiments, canola may be an edible rapeseed oil and containing a solid component having less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid, or a plant which produces such oil. The term canola includes transgenic and non-transgenic canola.

As used herein, reference to an oilseed plant or plants includes the plant and its progeny, such as its $F_1, F_2, F_3, F_4$, and subsequent generation plants. The plant or its progeny may be a hybrid. As used herein, a "line" or "breeding line" is a group of plants that display little or no genetic variation between individuals for at least one trait, such as a particular gene mutation or set of gene mutations. Such lines may be created by several generations of self-pollination and selection or by vegetative propagation from a single parent using tissue or cell culture techniques. A "variety" refers to a line that is used for commercial production and includes hybrid and open-pollinated varieties. As examples, the plant may include any of *Brassica*, flax, linseed, hemp, walnut, evening primrose, soy, sunflower, cotton, corn, olive, safflower, cocoa, peanut, hemp, *Camelina, crambe*, palm, coconut, sesame, castor bean, *lesquerella*, tallow, seanuts, tungnuts, kapok fruit, poppy, jojoba, *perilla*, or groundnut species. In various embodiments, the oilseed plant is a *Brassica* species or *Camelina* species. *Brassica* plants may include, for example, *B. napus, B. juncea*, and *B. rapa* (rapeseed) species, while *Camelina* species include, for example, *C. sativa*. The oilseed plant or oilseed crop plant may be canola. The phrase "hybrid plants" refers to plants which result from a cross between genetically different individuals. The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

In various embodiments, the growth stages of *Brassica* and other plants can, but are not required to, be understood according to the BBCH-scale, which lists growth stages including substages, from germination to harvest. For example, growth stages of canola plants may be understood according to the following growth stages from the BBCH-scale for canola:

Growth Stage 0—Germination
  00. dry seed (seed dressing takes place at this stage)
  01. seed imbibition (water absorption)
  03. seed imbibition complete
  05. radicle (root) emerges from seed
  06. elongation of root, formation of root hairs and/or lateral roots
  07. hypocotyl with cotyledons break though seed coat
  08. hypocotyl with cotyledons grow toward soil surface
  09. cotyledons break through soil surface
Growth Stage 1: Leaf Development
  10. cotyledons completely unfold
  11. first true leaf unfolds
  12. two leaves unfold
  13. three leaves unfold
  14. four leaves unfold
  15. five leaves unfold
  16. six leaves unfold
  17. seven leaves unfold
  18. eight leaves unfold
  19. nine or more leaves unfold
Growth Stage 2: Formation of Side Shoots
  20. No side shoots
  21. Beginning of side shoot development
  29. End of side shoot development
Growth Stage 3: Stem Elongation
  30. stem elongation (bolting) begins; or no internodes ("rosette")
  31. stem 10% of final length or 1 visibly extended internode
  32. stem 20% of final length or 2 visibly extended internode
  33. stem 30% of final length or 2 visibly extended internode
  34. stem 40% of final length or 2 visibly extended internode
  35. stem 50% of final length or 2 visibly extended internode
  36. stem 60% of final length or 2 visibly extended internode
  37. stem 70% of final length or 2 visibly extended internode
  38. stem 80% of final length or 2 visibly extended internode
  39. maximum stem length or 9 visibly extended internode
Growth Stage 4: (this BBCH Stage Omitted as it Relates to Booting)
Growth Stage 5: Inflorescence Emergence
  50. flower buds present, but still enclosed by leave
  51. flower buds visible from above (green bud)
  52. flower buds free, level with the youngest leaves
  53. flower buds raised above the youngest leaves
  55. individual flower buds (main inflorescence) visible but still closed
  58. individual flower buds (secondary inflorescence) visible but closed
  59. first petals visible, but flower buds still closed (yellow bud)
Growth Stage 6: Flowering
  60. first flowers open
  61. 10% of flowers on the main raceme open, main raceme elongating
  62. 20% of flowers on the main raceme open
  63. 30% of flowers open on the main raceme
  64. 40% of flowers on the main raceme open
  65. full flowering—50% of flowers on main raceme open, older petals falling
  67. flowering declining—majority of petals fallen
  69. flowering ends
Growth Stage 7: Development of Seed
  70. 0% of pods reach final size
  71. 10% of pods reach final size
  72. 20% of pods reach final size
  73. 30% of pods reach final size
  74. 40% of pods reach final size
  75. 50% of pods reach final size
  76. 60% of pods reach final size
  77. 70% of pods reach final size
  78. 80% of pods reach final size
  79—nearly all of the pods reach final size
Growth Stage 8: Ripening
  80. ripening begins—seed green, filling pod cavity
  81. 10% of pods ripe, seeds black and hard
  83. 30% of pods ripe, seeds black and hard
  85. 50% of pods ripe, seeds black and hard
  87. 70% of pods ripe, seeds black and hard
  89. fully ripe—nearly all pods ripe, seeds black and hard
Growth Stage 9: Senescence
  97. plants dead and dry
  99. harvested product The term "first flower" refers to time at which the first 10% of plants in a plurality of plants have flowered. In instances where 10% of plants cannot be determined, e.g., due to the plurality of plants having fewer than 10 plants, "first flower" can be understood as the first point in time when at least 10% of plants have flowered. For example, if the plurality of plants is 5 plants, first flower would be when a single plant has flowered. In various embodiments, "first flower" may correspond to BBCH-scale stage 6, substage 61.

The term "a period of seed maturation" as used herein can refer to a period from which the oilseeds first appear, through the period in which oilseeds grow and mature, and to the period when the plant is harvested. The period of seed maturation can also refer to a portion of such period. For example, in various embodiments, the period of seed maturation may correspond to BBCH-scale stage 7, BBCH-scale stage 8, BBCH-scale stages 7 and 8 taken together, or BBCH-scale stages 6, 7 and 8 taken together. As further examples, the period of seed maturation may be from first appearance of full sized pods to harvest, or it may be from first appearance of ripe pods to harvest, or it may be from first appearance of green seeds in pods until harvest. The period of seed maturation may start at BBCH-scale substage 50, 51, 52, 53, 54, 55, 56, 57, 58, 59, 60, 61, 62, 63, 64, 65, 66, 67, 68, 69, 70, 71, 72, 73, 74, 75, 75, 76, 77, 78, 79, 80, 81, 82, 83, 84, 85, 86, 87, 88, or 89, and the period of seed maturation may end at BBCH-scale substage 60, 61, 62, 63, 64, 65, 66, 67, 68, 69, 70, 71, 72, 73, 74, 75, 75, 76, 77, 78, 79, 80, 81, 82, 83, 84, 85, 86, 87, 88, 89, 90, 91, 92, 93, 94, 95, 96, 97, 98 or 99.

The present disclosure provides a method of increasing the proportion of long-chain omega-3 fatty acid in seed oil produced by a plurality of transgenic *Brassica* oilseed plants, comprising subjecting the transgenic *Brassica* oilseed plants to an environment which has an average daily day-night temperature difference of at least 13° C. during a period of seed maturation for the transgenic canola plants; and wherein the transgenic *Brassica* oilseed plants have been transgenically modified to produce seed oil comprising at least one of EPA, DHA and DPA.

The present disclosure also provides a method of cultivating a plurality of transgenic *Brassica* oilseed plants, comprising subjecting the transgenic *Brassica* oilseed plants to an environment which has an average daily day-night temperature difference of at least 13° C. during a period of seed maturation for the transgenic canola plants; and wherein the transgenic *Brassica* oilseed plants have been transgenically modified to produce seed oil comprising at least one of EPA, DHA and DPA.

In various embodiments, the *Brassica* oilseed plant may be canola. The *Brassica* oilseed plant may be a *B. napus, B. rapa, B. juncea, B. oleracea, B. nigra*, or *B. carinata*. The *Brassica* oilseed plant may comprise the LBFLFK and LBFDAU events.

In various embodiments, the average daily day-night temperature difference during the period of seed maturation is about 13° C., or 14° C. The average daily day-night temperature difference during the period of seed maturation may be from 13° C. to 15° C., from 13° C. to 17° C., or from 13° C. to 19° C. The average daily day-night temperature difference during the period of seed maturation may be at least 13° C., 15° C., 16° C., 17° C., 18° C., 19° C., or 20° C.

In various embodiments, the minimum daily day-night temperature difference during the period of seed maturation is about 13° C., 14° C., 15° C., 16° C., 17° C., 18° C., 19° C., or 20° C. The minimum daily day-night temperature difference during the period of seed maturation may be from 13° C. to 14° C. The minimum daily day-night temperature difference during the period of seed maturation may be at least 13° C., 14° C., 15° C., 16° C., 17° C., 18° C., 19° C., or 20° C.

In various embodiments, the average daily high-low temperature difference during the period of seed maturation is about 13° C., 14° C., 15° C., 16° C., 17° C., 18° C., 19° C., or 20° C. The average daily high-low temperature difference during the period of seed maturation may be from 13° C. to 15° C., from 13° C. to 17° C., or from 13° C. to 19° C. The average daily high-low temperature difference during the period of seed maturation may be at least 13° C., 14° C., 15° C., 16° C., 17° C., 18° C., 19° C., or 20° C.

In various embodiments, the minimum daily high-low temperature difference during the period of seed maturation is about 13° C., 14° C., 15° C., 16° C., 17° C., 18° C., 19° C., or 20° C. The minimum daily high-low temperature difference during the period of seed maturation may be from 13° C. to 15° C., from 13° C. to 17° C., or from 13° C. to 19° C. The minimum daily high-low temperature difference during the period of seed maturation may be at least 13° C., 14° C., 15° C., 16° C., 17° C., 18° C., 19° C., or 20° C.

In various embodiments, the period of seed maturation is from first flower to harvest. The period of seed maturation may be the period from first appearance of full sized pods to harvest. The period of seed maturation may be the period from first appearance of ripe pods to harvest. The period of seed maturation may be the period from appearance of green seeds in pods until harvest. The period of seed maturation may be the period during which seed pods fill.

In various embodiments, the period of seed maturation corresponds to BBCH-scale stage 7, BBCH-scale stage 8, BBCH-scale stages 7 and 8 taken together, or BBCH-scale stages 6, 7 and 8 taken together.

In various embodiments, the period of seed maturation starts at any one of BBCH-scale substages 50, 51, 52, 53, 54, 55, 56, 57, 58, 59, 60, 61, 62, 63, 64, 65, 66, 67, 68, 69, 70, 71, 72, 73, 74, 75, 75, 76, 77, 78, 79, 80, 81, 82, 83, 84, 85, 86, 87, 88, or 89 and ends at harvest.

In various embodiments, the environment is a growth chamber, a green house, a partially-enclosed outdoors environment or an open field. Where the environment is a growth chamber or a green house, temperature may be fully controlled via climate control. Where the environment is partially-enclosed outdoors environment or an open field, the temperature may be ambient air temperature. In various embodiments, the transgenic *Brassica* oilseed plants are planted in a field. The field may be at least 500 square feet. The field may be at least 1000 square feet. The field may be at least an acre. The field may be at least 10 acres. The field may be at least 100 acres. The field may be at least 1,000 acres.

In various embodiments, the seed oil is at least 5 wt % EPA. The seed oil can be at least 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % EPA. The seed oil can be about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % EPA. The seed oil can be up to 10 wt %, 15 wt %, 20 wt %, 25 wt % EPA. Hence, the seed oil can comprise between 5 wt % EPA and 25 wt % EPA.

In various embodiments, the seed oil is at least 1 wt % DPA. The seed oil can be at least 0.5 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % DPA. Hence, the seed oil can comprise between 1 wt % DPA and 20 wt % DPA.

In various embodiments, the seed oil is at least 0.2 wt % DHA. The seed oil can be at least 0.1 wt %, 0.2 wt %, 0.3 wt %, 0.4 wt %, 0.5 wt %, 0.6 wt %, 0.7 wt %, 0.8 wt %, 0.9 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % DHA. The seed oil can be about 0.1 wt %, 0.2 wt %, 0.3 wt %, 0.4 wt %, 0.5 wt %, 0.6 wt %, 0.7 wt %, 0.8 wt %, 0.9 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % DHA. The seed oil can be up to 10 wt %, 15 wt %, 20 wt %, 25 wt %, or 30 wt % DHA. Hence, the seed oil can comprise between 0.2 wt % DHA and 30 wt % DHA.

The seed oil can be at least 5.2 wt % a mixture of EPA and DHA. The seed oil can be at least 1 wt %, 2 wt %, 3 wt %, 4 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % EPA and DHA. The seed oil can be about 1 wt %, 2 wt %, 3 wt %, 4 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % EPA and DHA. Hence, the seed oil can comprise between 1 wt % and 20 wt % EPA and DHA.

In various embodiments, the seed oil is at least 6 wt % long chain omega-3 fatty acids. The seed oil can be at least 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % long chain omega-3 fatty acids. The seed oil can be about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, or 30 wt % long chain omega-3 fatty acids. Hence, the seed oil can comprise between 1 wt % long chain omega-3 fatty acids and 30 wt % long chain omega-3 fatty acids.

In various embodiments, the increased proportion of omega-3 fatty acid in seed oil is an increased proportion of long chain omega-3 fatty acids. The increased proportion of omega-3 fatty acid in seed oil can be an increased proportion of EPA and/or DHA omega-3 fatty acids. The increased proportion of omega-3 fatty acid in seed oil can be an increased proportion of EPA, DPA and DHA omega-3 fatty acids. The proportion of omega-3 fatty acid is increased in comparison to other transgenic Brassica oilseed plants under substantially identically conditions except the environment has an average daily day-night temperature difference of less than 7° C. during the period of seed maturation.

The present disclosure also provides canola seeds comprising seed oil having a high proportion of long chain omega-3 fatty acids. For example, the present disclosure provides canola seeds comprising seed oil having at least 17 wt % long chain omega-3 fatty acids. In various embodiments, the canola seeds may comprise seed oil having at least 6 wt % long chain omega-3 fatty acids. The seed oil can be at least 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % long chain omega-3 fatty acids. In various embodiments, the canola seeds may comprise seed oil having about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, or 30 wt % long chain omega-3 fatty acids based on total oil. In various embodiments, the canola seeds may comprise seed oil having up to 10 wt %, 15 wt %, 20 wt %, 25 wt %, 30 wt %, 35 wt %, or 40 wt % omega-3 fatty acids based on total oil. Hence, the canola seeds can comprise seed oil having 1 wt % to 40 wt % omega-3 fatty acids based on the total oil. Such canola seeds may be obtained by the methods of the present disclosure.

The actual percentage of the total oil from the transgenic oilseed plants that is EPA, DPA, or DHA may vary. In various embodiments, the transgenic oilseed plant seed oil contains at least 5% EPA, such as, for example 5-25% EPA or 5-15% EPA. The transgenic oilseed plant seed oil may comprise 5-6%, 6-7%, 7-8%, 8-9%, 9-10%, 10-15%, or >15% EPA. The transgenic oilseed plant seed oil may comprise DPA. The transgenic oilseed plant seed oil may comprise at least 1% DPA, such as at least 2% DPA, such as 1-10% DPA, 1-5% DPA, 2-5% DPA, or >10% DPA. In various embodiments, the oil contains 1-2% DPA, 2-3%, 3-4%, or 4-5% DPA. The transgenic oilseed plant seed oil may comprise is engineered to produce DHA. In various embodiments, the transgenic oilseed plant seed oil may comprise at least 0.5% DHA, such as at least 1% DHA, such as 1-2%, 2-3%, 3-4%, 1-4%, 1-5%, or >5% DHA.

In various embodiments, the EPA+DHA content of the oil is, for example, at least 6%, such as 6-50%, such as 6-30%, such as 6-15%, such as 8-15%, such as 8.5-13.5%. In various embodiments, the EPA+DHA content is 6-8%, in others it is 8-10%, in others it is 10-12%, an in still others it is 12-14%. In various embodiments, the EPA+DHA content of the seed oil is tailored to a specific percentage by mixing the oil from the modified plants with oil from plants of the same or similar species that do not produce long-chain omega-3 fatty acids. This way, for example, the amount of EPA and DHA can be controlled without significantly altering the percentages of other fatty acids in the oil.

In various embodiments, the amount of EPA+DPA+DHA in the seed oil is, for example, at least 8%, such as between 8 and 50%, such as 8-40%, such as 8-20%, such as 10-20%, such as 10-15%, 15-20% or >20%.

The present disclosure thus provides a method of cultivating a plurality of transgenic canola plants, comprising growing the transgenic canola plants in an environment which has an average daily day-night temperature difference of at least 7° C. during a period of seed maturation for the transgenic canola plants; and wherein the transgenic canola plants produce a seed oil comprising at least one of EPA, DHA and DPA.

EXAMPLES

Various embodiments of the present disclosure can be better understood by reference to the following Examples which are offered by way of illustration. The present disclosure is not limited to the Examples given herein.

Hybrids A-C

Hybrids A-C are transgenic Brassica oilseed plants, namely, canola F1 hybrids which are each transgenically modified to contain the event LBFLFK. Hybrids A-C were prepared by introgression of the LBFLFK event into standard canola backgrounds of Cargill Incorporated. (see e.g.; WO 2016/075303, WO 2016/075325 and WO 2016/075327).

TABLE 1

| Name | Hybrid |
|---|---|
| Hybrid A | 11CA2034.014/04CF80.69*3/LBFLFK |
| Hybrid B | 11CA2034.014/09CF126.027*3/LBFLFK |
| Hybrid C | 11CA2034.014/10CF635.003*3/LBFLFK |

For growth chamber experiments, plants were grown in PGC-20 growth chambers (Conviron) on a 16/8 hour day/night cycle. Plants were fertilized from germination through end of flowering with 100 ppm Jack's® 20-20-20 and were bottom watered as needed to keep soil moist. Plants were grown from germination until flowering at 22° C./19° C. day/night temperature, at flowering the temperature was switched to the temperature treatments of either 15° C./12° C., 22° C./19° C. or 25° C./12° C. in separate PGC-20 growth chambers through maturity, the point at which all seeds in all pods had undergone complete color change from green to brown. At flowering, plants were bagged individually and were allowed to self-pollinate. Pods were harvested from individual plants, bulked as a single plant, and sub-sampled for fatty acid profiling of ~30 seeds. For Hybrid A and C, 10 plants were grown at each temperature treatment. For Hybrid B, 6-8 plants were grown for each temperature treatment.

Fatty acid profile of seed was measured by gas chromatography using ~30 seeds and standard fatty acid methyl ester preparation (adapted from AOCS method Ce 1-62) immediately following crushing. GLC-566 (NuChek Prep) was used for the standard and fatty acid profiles were determined by ChemStation software (Agilent) as a percent of total fatty acids. The fatty acid composition of seeds was determined by a modification of American Oil Chemist's Society (AOCS) protocol Ce 1-62. In the procedure fatty acids present as acylglycerols are converted to fatty acid methyl esters, which are analyzed by gas liquid chromatography (GLC or GC). For each sample to be analyzed 20-30 seeds are placed in a 15 ml centrifuge tube along with two steel ball bearings. The tube is capped and shaken for 30 seconds or until the seeds are visibly crushed. Approximately 0.6 mL of 2 N KOH in methanol is added to the tube, and the tube is shaken again for approximately one minute. The tube and its contents are placed in a water bath at 70±5° C. for 2 min. After removing the tube from the bath 4 mL of water saturated with sodium chloride and 2.0 mL of isooctane with 100 ppm of BHT are added, the tube is shaken and centrifuged for 1 min in a tabletop centrifuge. A portion of the isooctane supernatant is transferred to a gas chromatographic (GC) vial and capped. Vials are stored at 0-4° C. until analysis, but no more than five days. Fatty acid methyl esters were subject to analysis on a GC on an instrument equipped with a 20 m×0.18 mm×0.2 μm DB-225 (50% Cyanopropylphenyl) column from Agilent Technologies with an injector temperature of 250° C. and 1 μl is injected with a split of 50:1 using 0.8 ml/min Hydrogen column flow (constant flow mode). Initial temperature is 190° C./0 min->15 C.°/min->220° C.->220° C./9 min. and a flame ionization detector. The instrument is calibrated with a fatty acid methyl ester standard, such as NuChek Prep Catalog number GLC 566. The content of fatty acids having from 14 carbon atoms (C14 fatty acids) to 24 carbon atoms (C24 fatty acids) is determined using the integrated peak area for each type of fatty acid reported normalized to the total peak area for those fatty acids.

Cultivation

*Brassica* oilseed plants can be grown using conventional growing techniques for *Brassica* oilseed plants. The plants may be grown in growth chambers, greenhouses, partially-enclosed field and in open field.

Harvest

Harvest can be performed according to conventional techniques used for oilseed plants. For example, harvest can be performed via direct combining or via swathing. Swathing can be performed by cutting the crop and laying windrows directly on the cut stubble using any of self-propelled or power-take-off driven pull-type swathers with draper belt style or auger style windrowers. The cut crop is permitted to dry to a uniform seed moisture content, approximately five to 10 days after cutting. In comparison to direct combining, swathing may be performed eight to ten days earlier. On a growth chamber scale, for example, harvesting may be performed manually by hand.

Seed Oil Collection

Seed Oil can be obtained using conventional canola seed crushing processes which include tempering, flaking, flake conditioning, expeller pressing and filtering.

Oil Analysis

Oil analysis can be performed as described in the standard literature including Ullman, Encyclopedia of Industrial Chemistry, Bd. A2, S. 89-90 und S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Belter, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 1 1, S. 1-27, VCH: Weinheim; and Dechow, F. J. (1989) Separation and purification techniques in biotechnology, Noyes Publications. It is acknowledged that extraction of lipids and fatty acids can be carried out using other protocols than those cited above, such as described in Cahoon et al. (1999) Proc. Natl. Acad. Sci. USA 96 (22): 12935-12940 and Browse et al. (1986) Analytic Biochemistry 152: 141-145. The protocols used for quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

Example 1—Seed Maturation Temperature Test at 15° C. Day/12° C. Night

Hybrids A-C were grown in growth chambers. The environment in the growth chambers was controlled to mimic a day-night temperature cycle. During the period of seed maturation, the plants were subjected to a day temperature of 15° C. and a night temperature of 12° C. Results for Hybrid A at 15° C./12° C. during seed maturation are shown in Table 1. Results for Hybrid B at 15° C./12° C. during seed maturation are shown in Table 2. Results for Hybrid C at 15° C./12° C. during seed maturation are shown in Table 3.

TABLE 2

| Hybrid | Temperature Treatment | Total Oil % | % EPA in oil | % DPA in oil | % DHA in oil | % EPA, DPA and DHA in oil |
|---|---|---|---|---|---|---|
| Hybrid A | 15° C./12° C. | 37.609 | 12.69 | 3.10 | 0.89 | 16.68 |
| Hybrid A | 15° C./12° C. | 40.408 | 11.20 | 3.06 | 0.67 | 14.93 |
| Hybrid A | 15° C./12° C. | 41.716 | 10.40 | 3.09 | 0.68 | 14.17 |
| Hybrid A | 15° C./12° C. | 41.825 | 11.83 | 3.00 | 0.74 | 15.57 |
| Hybrid A | 15° C./12° C. | 42.811 | 9.60 | 2.76 | 0.54 | 12.90 |
| Hybrid A | 15° C./12° C. | 44.344 | 7.70 | 2.16 | 0.59 | 10.45 |
| Hybrid A | 15° C./12° C. | 46.891 | 7.73 | 2.20 | 0.37 | 10.31 |
| Hybrid A | 15° C./12° C. | 47.219 | 5.84 | 1.83 | 0.38 | 8.05 |
| Hybrid A | 15° C./12° C. | 47.294 | 6.84 | 1.64 | 0.64 | 9.11 |
| Hybrid A | 15° C./12° C. | 47.616 | 7.51 | 1.90 | 0.42 | 9.83 |

TABLE 3

| Hybrid | Temperature Treatment | Total Oil % | % EPA in oil | % DPA in oil | % DHA in oil | % EPA, DPA and DHA in oil |
|---|---|---|---|---|---|---|
| Hybrid B | 15° C./12° C. | 42.677 | 11.30 | 2.55 | 0.71 | 14.56 |
| Hybrid B | 15° C./12° C. | 43.626 | 10.46 | 2.28 | 0.60 | 13.34 |
| Hybrid B | 15° C./12° C. | 44.55 | 10.25 | 2.65 | 0.48 | 13.38 |
| Hybrid B | 15° C./12° C. | 45.556 | 8.78 | 2.06 | 0.50 | 11.33 |
| Hybrid B | 15° C./12° C. | 46.553 | 8.70 | 2.15 | 0.44 | 11.30 |
| Hybrid B | 15° C./12° C. | 46.828 | 9.17 | 2.38 | 0.48 | 12.03 |
| Hybrid B | 15° C./12° C. | 47.491 | 8.02 | 1.85 | 0.47 | 10.35 |
| Hybrid B | 15° C./12° C. | 48.387 | 7.77 | 1.97 | 0.40 | 10.14 |

TABLE 4

| Hybrid | Temperature Treatment | Total Oil % | % EPA in oil | % DPA in oil | % DHA in oil | % EPA, DPA and DHA in oil |
|---|---|---|---|---|---|---|
| Hybrid C | 15° C./12° C. | 38.022 | 9.49 | 3.24 | 0.00 | 12.73 |
| Hybrid C | 15° C./12° C. | 40.78 | 10.30 | 2.77 | 0.67 | 13.74 |
| Hybrid C | 15° C./12° C. | 41.181 | 9.36 | 2.55 | 0.55 | 12.46 |
| Hybrid C | 15° C./12° C. | 41.448 | 8.95 | 2.45 | 0.51 | 11.91 |
| Hybrid C | 15° C./12° C. | 41.926 | 8.24 | 2.22 | 0.55 | 11.02 |
| Hybrid C | 15° C./12° C. | 42.522 | 9.76 | 2.50 | 0.60 | 12.85 |
| Hybrid C | 15° C./12° C. | 45.161 | 8.40 | 2.21 | 0.52 | 11.13 |
| Hybrid C | 15° C./12° C. | 45.908 | 6.85 | 1.91 | 0.51 | 9.27 |
| Hybrid C | 15° C./12° C. | 46.296 | 6.54 | 2.01 | 0.32 | 8.86 |
| Hybrid C | 15° C./12° C. | 49.66 | 5.15 | 1.53 | 0.30 | 6.98 |

Example 2—Seed Maturation Temperature Test at 22° C. Day/19° C. Night

Hybrid A-C were grown in growth chambers. The environment in the growth chambers was controlled to mimic a day-night temperature cycle. During the period of seed maturation, the plants were subjected to a day temperature of 22° C. and a night temperature of 19° C. Results for Hybrid A at 22° C./19° C. during seed maturation are shown in Table 5. Results for Hybrid B at 22° C./19° C. during seed maturation are shown in Table 6. Results for Hybrid C at 22° C./19° C. during seed maturation are shown in Table 7.

TABLE 5

| Hybrid | Temperature Treatment | Total Oil % | % EPA in oil | % DPA in oil | % DHA in oil | % EPA, DPA and DHA in oil |
|---|---|---|---|---|---|---|
| Hybrid A | 22° C./19° C. | 36.157 | 8.99 | 2.79 | 0.54 | 12.32 |
| Hybrid A | 22° C./19° C. | 37.503 | 8.92 | 2.67 | 0.61 | 12.20 |
| Hybrid A | 22° C./19° C. | 38.662 | 10.48 | 3.01 | 0.51 | 14.00 |
| Hybrid A | 22° C./19° C. | 38.961 | 10.26 | 2.81 | 0.64 | 13.71 |
| Hybrid A | 22° C./19° C. | 39.868 | 10.76 | 2.88 | 0.57 | 14.21 |
| Hybrid A | 22° C./19° C. | 40.681 | 9.76 | 2.56 | 0.55 | 12.87 |
| Hybrid A | 22° C./19° C. | 41.559 | 9.12 | 2.85 | 0.40 | 12.38 |
| Hybrid A | 22° C./19° C. | 42.782 | 8.29 | 2.35 | 0.54 | 11.19 |
| Hybrid A | 22° C./19° C. | 43.172 | 9.36 | 2.33 | 0.52 | 12.21 |
| Hybrid A | 22° C./19° C. | 44.589 | 5.81 | 1.79 | 0.37 | 7.96 |

TABLE 6

| Hybrid | Temperature Treatment | Total Oil % | % EPA in oil | % DPA in oil | % DHA in oil | % EPA, DPA and DHA in oil |
| --- | --- | --- | --- | --- | --- | --- |
| Hybrid B | 22° C./19° C. | 39.283 | 9.06 | 2.55 | 0.51 | 12.12 |
| Hybrid B | 22° C./19° C. | 42.427 | 9.71 | 2.62 | 0.55 | 12.87 |
| Hybrid B | 22° C./19° C. | 42.935 | 7.96 | 2.43 | 0.44 | 10.83 |
| Hybrid B | 22° C./19° C. | 44.198 | 8.10 | 2.23 | 0.38 | 10.70 |
| Hybrid B | 22° C./19° C. | 44.236 | 8.91 | 2.26 | 0.44 | 11.61 |
| Hybrid B | 22° C./19° C. | 45.919 | 9.37 | 2.14 | 0.48 | 11.99 |

TABLE 7

| Hybrid | Temperature Treatment | Total Oil % | % EPA in oil | % DPA in oil | % DHA in oil | % EPA, DPA and DHA in oil |
| --- | --- | --- | --- | --- | --- | --- |
| Hybrid C | 22° C./19° C. | 37.725 | 9.27 | 2.87 | 0.56 | 12.70 |
| Hybrid C | 22° C./19° C. | 38.898 | 7.88 | 2.39 | 0.43 | 10.69 |
| Hybrid C | 22° C./19° C. | 39.98 | 7.29 | 1.73 | 0.80 | 9.82 |
| Hybrid C | 22° C./19° C. | 43.397 | 8.29 | 2.43 | 0.49 | 11.20 |
| Hybrid C | 22° C./19° C. | 44.275 | 7.73 | 2.25 | 0.42 | 10.40 |
| Hybrid C | 22° C./19° C. | 44.804 | 6.93 | 2.09 | 0.46 | 9.48 |
| Hybrid C | 22° C./19° C. | 44.948 | 7.14 | 2.16 | 0.32 | 9.62 |
| Hybrid C | 22° C./19° C. | 46.113 | 6.17 | 1.92 | 0.28 | 8.37 |
| Hybrid C | 22° C./19° C. | 47.76 | 6.05 | 1.80 | 0.33 | 8.17 |
| Hybrid C | 22° C./19° C. | 48.501 | 5.81 | 1.85 | 0.26 | 7.93 |

Example 3—Seed Maturation Temperature Test at 25° C. Day/12° C. Night

Hybrids A-C were grown in growth chambers. The environment in the growth chambers was controlled to mimic a day-night temperature cycle. During the period of seed maturation, the plants were subjected to a day temperature of 25° C. and a night temperature of 12° C. Results for Hybrid A at 25° C./12° C. during seed maturation are shown in Table 8. Results for Hybrid B at 25° C./12° C. during seed maturation are shown in Table 9. Results for Hybrid C at 25° C./12° C. during seed maturation are shown in Table 10.

TABLE 8

| Hybrid | Temperature Treatment | Total Oil % | % EPA in oil | % DPA in oil | % DHA in oil | % EPA, DPA and DHA in oil |
| --- | --- | --- | --- | --- | --- | --- |
| Hybrid A | 25° C./12° C. | 37.432 | 12.66 | 3.04 | 0.88 | 16.58 |
| Hybrid A | 25° C./12° C. | 37.484 | 12.69 | 3.16 | 0.79 | 16.64 |
| Hybrid A | 25° C./12° C. | 38.856 | 12.50 | 3.14 | 0.90 | 16.55 |
| Hybrid A | 25° C./12° C. | 39.775 | 11.48 | 3.06 | 0.77 | 15.31 |
| Hybrid A | 25° C./12° C. | 40.389 | 11.74 | 2.93 | 0.76 | 15.44 |
| Hybrid A | 25° C./12° C. | 41.208 | 10.17 | 2.41 | 0.70 | 13.28 |
| Hybrid A | 25° C./12° C. | 42.148 | 11.03 | 2.74 | 0.76 | 14.53 |
| Hybrid A | 25° C./12° C. | 42.249 | 10.69 | 2.84 | 0.64 | 14.17 |
| Hybrid A | 25° C./12° C. | 42.785 | 10.95 | 2.43 | 0.85 | 14.23 |
| Hybrid A | 25° C./12° C. | 45.883 | 9.50 | 2.37 | 0.59 | 12.46 |

TABLE 9

| Pedigree | Temperature Treatment | Total Oil % | % EPA in oil | % DPA in oil | % DHA in oil | % EPA, DPA and DHA in oil |
| --- | --- | --- | --- | --- | --- | --- |
| Hybrid B | 25° C./12° C. | 38.306 | 13.85 | 3.13 | 0.97 | 17.96 |
| Hybrid B | 25° C./12° C. | 40.978 | 12.38 | 2.84 | 0.80 | 16.01 |
| Hybrid B | 25° C./12° C. | 41.296 | 12.10 | 2.57 | 0.70 | 15.37 |
| Hybrid B | 25° C./12° C. | 44.077 | 11.33 | 2.61 | 0.79 | 14.73 |
| Hybrid B | 25° C./12° C. | 44.95 | 9.77 | 2.25 | 0.69 | 12.71 |
| Hybrid B | 25° C./12° C. | 46.227 | 9.65 | 2.06 | 0.58 | 12.30 |

TABLE 10

| Hybrid | Temperature Treatment | Total Oil % | % EPA in oil | % DPA in oil | % DHA in oil | % EPA, DPA and DHA in oil |
|---|---|---|---|---|---|---|
| Hybrid C | 25° C./12° C. | 38.002 | 9.02 | 2.31 | 0.61 | 11.94 |
| Hybrid C | 25° C./12° C. | 38.185 | 9.80 | 2.47 | 0.65 | 12.92 |
| Hybrid C | 25° C./12° C. | 38.564 | 9.04 | 2.31 | 0.62 | 11.97 |
| Hybrid C | 25° C./12° C. | 39.295 | 8.61 | 2.27 | 0.48 | 11.36 |
| Hybrid C | 25° C./12° C. | 39.799 | 10.30 | 2.61 | 0.79 | 13.70 |
| Hybrid C | 25° C./12° C. | 40.564 | 10.84 | 2.56 | 0.86 | 14.26 |
| Hybrid C | 25° C./12° C. | 40.713 | 7.69 | 2.16 | 0.38 | 10.22 |
| Hybrid C | 25° C./12° C. | 40.841 | 7.52 | 2.06 | 0.43 | 10.01 |
| Hybrid C | 25° C./12° C. | 41.213 | 9.10 | 2.43 | 0.61 | 12.14 |
| Hybrid C | 25° C./12° C. | 46.68 | 7.66 | 1.82 | 0.44 | 9.92 |

Discussion

Examples 1-3 unexpectedly showed that for each of three different transgenic *Brassica* hybrids, day/night temperatures cycles having greater extremes resulted in a higher proportion of long chain omega-3 fatty acids in the seed oil produced therefrom, notably EPA, DPA and DHA. See, Table 11 and FIG. 1, which provide a summary of the results set forth in Tables 2-10. Hybrid A provided consistent results at overall lower temperature (15° C./12° C.) as it did at overall higher temperatures (22° C./19° C.). Hybrid B provided similar results, but higher temperature had the effect of slightly reducing the proportion of omega-3. Hybrid C showed a significant reduction in the proportion of omega-3 produced. These results make it even more surprising that increasing the day temperature to 25° C. and lowering the night temperature to 12° C. resulted in increased percentage of omega-3 fatty acid in the seed oil.

TABLE 11

| Hybrid | Temperature Treatment | Average % Omega 3 | St dev |
|---|---|---|---|
| Hybrid A | 15° C./12° C. | 12.20 | 3.02 |
| Hybrid A | 22° C./19° C. | 12.30 | 1.79 |
| Hybrid A | 25° C./12° C. | 14.92 | 1.44 |
| Hybrid B | 15° C./12° C. | 12.05 | 2.12 |
| Hybrid B | 22° C./19° C. | 11.69 | 1.49 |
| Hybrid B | 25° C./12° C. | 14.84 | 1.51 |
| Hybrid C | 15° C./12° C. | 11.10 | 1.58 |
| Hybrid C | 22° C./19° C. | 9.84 | 0.83 |
| Hybrid C | 25° C./12° C. | 11.84 | 2.11 |

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

ADDITIONAL EMBODIMENTS

The following exemplary embodiments are provided, the numbering of which is not to be construed as designating levels of importance:

Embodiment 1. provides a method of increasing the proportion of long-chain omega-3 fatty acid in seed oil produced by a plurality of transgenic *Brassica* oilseed plants, comprising subjecting the transgenic *Brassica* oilseed plants to an environment which has an average daily day-night temperature difference of at least 7° C. during a period of seed maturation for the transgenic canola plants; and wherein the transgenic *Brassica* oilseed plants have been transgenically modified to produce seed oil comprising at least one of EPA, DHA and DPA.

Embodiment 2. provides a method of cultivating a plurality of transgenic *Brassica* oilseed plants, comprising growing the transgenic *Brassica* oilseed plants in an environment which has an average daily day-night temperature difference of at least 7° C. during a period of seed maturation for the transgenic canola plants; and wherein the transgenic canola plants produce seeds comprising at least one of EPA, DHA and DPA.

Embodiment 3. provides the method of any one of Embodiments 1-2, wherein the *Brassica* oilseed plants are canola.

Embodiment 4. provides the method of any one of Embodiments 1-3, wherein the average daily day-night temperature difference is about 13° C.

Embodiment 5. provides the method of any one of Embodiments 1-4, wherein the environment has a minimum daily day-night temperature difference of at least 7° C. during the period of seed maturation for the transgenic *Brassica* oilseed plants.

Embodiment 6. provides the method of any one of Embodiments 1-5, wherein the period of seed maturation is from first flower to harvest.

Embodiment 7. provides the method of any one of Embodiments 1-5, wherein the period of seed maturation is from first appearance of full sized pods to harvest.

Embodiment 8. provides the method of any one of Embodiments 1-5, wherein the period of seed maturation is from first appearance of ripe pods to harvest.

Embodiment 9. provides the method of any one of Embodiments 1-5, wherein the period of seed maturation is from first appearance of green seeds in pods until harvest.

Embodiment 10. provides the method of any one of Embodiments 1-9, wherein the environment is a growth chamber, a green house, a partially-enclosed outdoors environment or an open field.

Embodiment 11. provides the method of any one of Embodiments 1-10, wherein the transgenic *Brassica* oilseed plants are planted in a field.

Embodiment 12. provides the method of Embodiment 11 wherein the field is at least an acre.

Embodiment 13. provides the method of any one of Embodiments 1-12, wherein the seed oil is at least 5 wt % EPA.

Embodiment 14. provides the method of any one of Embodiments 1-13, wherein the seed oil is at least 1 wt % DPA.

Embodiment 15. provides the method of any one of Embodiments 1-14, wherein the seed oil is at least 0.2 wt % DHA.

Embodiment 16. provides the method of any one of Embodiments 1-15, wherein the seed oil is at least 5.2 wt % a mixture of EPA and DHA.

Embodiment 17. provides the method of any one of Embodiments 1-16, wherein the seed oil is at least 14 wt % a mixture of EPA and DHA.

Embodiment 18. provides the method of any one of Embodiments 1-17, wherein the seed oil is at least 6 wt % long chain omega-3 fatty acids.

Embodiment 19. provides the method of any one of Embodiments 1-18, wherein the seed oil is at least 17 wt % long chain omega-3 fatty acids.

Embodiment 20. provides the method of any one of Embodiments 1-19, wherein the proportion of omega-3 fatty acid in the seed oil is increased in comparison to transgenic Brassica oilseed plants grown under substantially identically conditions except subjected to an environment which has an average daily day-night temperature difference of less than 7° C. during the period of seed maturation.

Embodiment 21. provides Brassica oilseed plant seeds obtained from the method of any one of Embodiments 1-20.

Embodiment 22. provides Brassica oilseed plant seeds comprising seed oil which is at least 17 wt % long chain omega-3 fatty acids.

Embodiment 23. provides canola seeds comprising seed oil which is at least 17 wt % long chain omega-3 fatty acids.

Embodiment 24. provides oil obtained from the seeds of any one of Embodiments 21-24.

Embodiment 25 provides the method of any one or any combination of Embodiments 1-20, or a plant, seed or oil produced therefrom, or the seeds of Embodiments 21-24 optionally configured such that all elements or options recited, and each permutation thereof, are available to use or select therefrom.

What is claimed is:

1. A method of increasing the proportion of long-chain omega-3 fatty acids in seed oil produced by a plurality of transgenic *Brassica napus* oilseed plants, comprising growing said transgenic *Brassica napus* oilseed plants at a daytime temperature of about 25° C., and a nighttime temperature of about 12° C., wherein said growing is for a period of seed maturation for said transgenic *Brassica napus* oilseed plants, wherein said period of seed maturation comprises BBCH-scale growth stage 6, BBCH-scale growth stage 7 and BBCH-scale growth stage 8 of *Brassica napus* oilseed plant growth stages, wherein said transgenic *Brassica napus* oilseed plants have been transgenically modified to produce said seed oil comprising at least one of EPA, DHA, and DPA, and wherein the proportion of long-chain omega-3 fatty acids in said seed oil produced by said transgenic *Brassica napus* oilseed plants is increased corresponding to controls of *Brassica napus* oilseed plants.

2. The method of claim 1, wherein said transgenic *Brassica napus* oilseed plants are grown in a growth chamber, a green house, a partially-enclosed outdoors environment, or an open field.

3. The method of claim 1, wherein said transgenic *Brassica napus* oilseed plants are grown in a field.

4. The method of claim 1, wherein said seed oil is at least 5 wt % EPA.

5. The method of claim 1, wherein said seed oil is at least 1 wt % DPA.

6. The method of claim 1, wherein said seed oil is at least 0.2 wt % DHA.

7. The method of claim 1, wherein said seed oil is at least 5.2 wt % a mixture of EPA and DHA.

8. The method of claim 1, wherein said seed oil is at least 6 wt % long chain omega-3 fatty acids.

9. The method of claim 1, wherein said seed oil comprises between 5 wt % EPA and 25 wt % EPA.

10. The method of claim 1, wherein said seed oil comprises between 1 wt % DPA and 20 wt % DPA.

11. The method of claim 1, wherein said seed oil comprises between 0.2 wt % DHA and 30 wt % DHA.

12. The method of claim 1, wherein said seed oil comprises between 1 wt % and 20 wt % of a mixture of EPA and DHA.

13. The method of claim 1, wherein said seed oil comprises between 1 wt % long chain omega-3 fatty acids and 30 wt % long chain omega-3 fatty acids.

* * * * *